(12) United States Patent
Langenbacher et al.

(10) Patent No.: US 7,064,816 B2
(45) Date of Patent: Jun. 20, 2006

(54) REFRACTOMETER

(75) Inventors: Markus Langenbacher, Lenzkirch (DE); Andreas Derr, Wutöschingen (DE); Frank Eder, Stühlingen (DE)

(73) Assignee: Testo AG, Lenzkirch (DE)

( * ) Notice: Subject to any disclaimer, the term of this patent is extended or adjusted under 35 U.S.C. 154(b) by 273 days.

(21) Appl. No.: 10/476,749

(22) PCT Filed: Dec. 19, 2002

(86) PCT No.: PCT/EP02/14586
§ 371 (c)(1),
(2), (4) Date: Nov. 3, 2003

(87) PCT Pub. No.: WO03/060492
PCT Pub. Date: Jul. 24, 2003

(65) Prior Publication Data
US 2004/0125363 A1    Jul. 1, 2004

(30) Foreign Application Priority Data
Jan. 21, 2002  (DE) ................................ 102 02 117

(51) Int. Cl.
*G01N 21/41* (2006.01)

(52) U.S. Cl. ...................... 356/128; 356/133; 356/134; 356/135

(58) Field of Classification Search ......... 356/128–137
See application file for complete search history.

(56) References Cited

U.S. PATENT DOCUMENTS

| | | |
|---|---|---|
| 3,487,069 A | 12/1969 | Maselli |
| 4,997,278 A | 3/1991 | Finlan et al. |
| 6,149,591 A | 11/2000 | Henderson et al. |
| 2001/0035950 A1 | 11/2001 | Nicholas |

FOREIGN PATENT DOCUMENTS

| | | |
|---|---|---|
| DE | 90 15 539 | 1/1991 |
| DE | 100 07 818 A1 | 8/2001 |

*Primary Examiner*—Gregory J. Toatley, Jr.
*Assistant Examiner*—Amanda Merlino
(74) *Attorney, Agent, or Firm*—Muirhead and Saturnelli LLC

(57) ABSTRACT

The invention relates to a portable refractometer comprising a depression (7) for samples, located on an insertion tip (11) in such a way that once the insertion tip (11) has penetrated a liquid or a fruit, a sufficient quantity of the sample liquid remains in the depression (7) for samples, thus wetting a measuring surface (4) that is delimited in said depression by a transparent body. The refractive index of the wetting liquid can be determined by measuring the intensity of an optical beam that is reflected by the measuring surface (4).

16 Claims, 3 Drawing Sheets

REFRACTOMETER

BACKGROUND OF THE INVENTION

1. Technical Field

The present invention relates to a refractometer for determining the refractive index of a liquid and, optionally, variables derived therefrom such as, for example, a sugar concentration, having a sensor system which has a radiation source for generating a measuring beam, a beam detector for detecting the measuring beam, and a measuring path to be traveled by the measuring beam, on which path a measuring surface to be wetted by the liquid and which interacts with the measuring beam is situated.

2. Description of the Related Art

Such refractometers are used as digital or analog measuring instruments, for example, for determining the concentration of certain substances dissolved in a liquid and influencing the refractive index. For example, in winemaking, the determination of the sugar content in the grape juice is an important area of application of such measurements.

Two types of measuring instruments are basically known in this area; one requires a sample to be taken and introduced into the measuring instrument, for example, drop by drop, while the other design provides for the immersion of a sensor into the analyte, i.e., into the liquid, to perform the measurement.

Sampling in the case of the first above-named variant is relatively complicated and time-consuming, and the instrument must be thoroughly cleaned before each sampling. In the instrument of the second variant, the problem often arises that the refractometer has a temperature which is different from that of the analyte, so that the required temperature compensation in determining the temperature-dependent refractive index is very difficult to perform. Furthermore, it may be difficult to take into account the effect of external light in optical measurements when a probe is introduced into the substance to be analyzed.

U.S. Pat. No. 5,859,696 describes a refractometer of a type similar to the one mentioned previously for determining the sugar content in a liquid, in which an optical beam is emitted by a radiation source, is reflected inside a transparent body on a measuring surface, and returned into a beam detector. If the measuring surface is wetted on the outside with a liquid having a high refractive index, for example, a soft drink having a high sugar concentration, this results in the refractive index of the liquid on the measuring surface approaching the refractive index of the transparent body and thus in a weaker reflection of the beam on the measuring surface or, in other words, in most of the beam penetrating the measuring surface and entering the liquid, so that the intensity of the reflected beam is greatly reduced. This is detected optically and a high or low sugar concentration is obtained as a function of the measured intensity of the reflected beam. The instrument is usable in a simple manner by immersing a measuring tip into the liquid and detecting the corresponding signal on the portable instrument. The temperature of the liquid is not taken into account in the measurement.

Accordingly, it is desirable to refine a refractometer of a simple construction of the above-mentioned type in such a way that a simple and rapid handling is made possible, while effective temperature compensation is ensured.

According to the present invention, a refractometer is disclosed in which the measuring surface is situated in a depression for samples of an insertion probe which is insertable into the liquid. The design according to the present invention makes it possible to use the insertion probe, which is insertable into the liquid and containing the depression for samples, for sampling and measurement, the refraction number, i.e., the refractive index, being determined in the depression after sampling the liquid to be measured. Only a small volume of liquid remains in the depression for samples; therefore the temperature between the insertion probe and the liquid is rapidly equalized, so that the refractometer and the liquid have the same temperature at the time of the measurement. Furthermore, temperature compensation is made simple by measuring the temperature at the probe. For this purpose, a temperature sensor may be placed within the insertion probe.

To take a new sample of the same or a different liquid, it is sufficient to insert the insertion probe into a liquid again; optionally, the depression for samples may be briefly cleaned beforehand if this seems to be necessary when handling liquids to be measured. Otherwise, it is also conceivable to simply introduce the probe into the liquid again, the liquid measured in the first measurement being simply washed out of the depression for samples by the second liquid.

Sampling and, optionally also, repeated use of the refractometer according to the present invention in a measurement is considerably simplified, and effective temperature compensation is made possible. For example, the insertion probe may have a tip at its end to make insertion into relatively large fruits possible to directly measure the fruit juice inside. The surface of the insertion probe may also have a groove through which the liquid to be measured may flow into the depression for samples after brief insertion through the liquid surface or into a fruit.

An advantageous embodiment of the present invention provides for the measuring surface to be delimited by a lens body.

The lens body is situated in such a way that one side is wettable by the liquid and on the other side the lens body surface is kept free of the liquid. The radiation source and the beam detector are then placed on the side of the lens body which is kept free of the liquid, permitting the measuring beam from the radiation source to impinge on the lens body, to be at least partially reflected there on the measuring surface wetted with the liquid, and to be subsequently directed to the beam detector. The intensity of the reflected measuring beam is then a function of the ratio between the refractive index of the lens body and that of the wetting liquid. The design of the geometry of the lens body is preferably such that the measuring beam is bundled or remains bundled in the lens body, and a suitable arrangement of the radiation source and the beam detector with respect to the lens body may be selected.

According to another advantageous embodiment of the present invention, the measuring surface is delimited by a glass body.

In principle, the fact that the measuring surface is delimited by a glass body means that cleaning of the measuring surface after performing the measurement is simplified without scratching the measuring surface. In addition, effective temperature equalization between the sensor system and the liquid is ensured by the relatively good thermal conductivity of glass.

With respect to the stability of the mechanical construction, the present invention is advantageously designed in such a way that the radiation source, the beam detector, and the lens body or, as the case may be, the glass body, are held in a metallic mount, which is made of steel or aluminum in particular.

The design of the mount made of a stable material in the form of steel or aluminum results in the geometrical configuration of the radiation source, detector, and lens being sufficiently stable to the point that even impacts will not alter the measuring path. The metallic design also makes rapid and effective temperature equalization between the individual elements of the sensor system and the liquid in the depression for samples possible. Temperature equalization may be improved by contact between the liquid and the metallic mount.

It is also advantageous to integrate a temperature sensor into the area of the sensor system. In this way the temperature of the sensor system and of the liquid may be measured at the same time as the temperature-dependent refractive index after these temperatures have adjusted to one another, which occurs after a few seconds. The measured refractive index of the liquid may then be recalculated to a normalized temperature in an analyzer, taking into account for the compensation the measured temperature. Because only a single temperature is to be taken into account with the sensor system according to the present invention, the calibration of the sensor system is also greatly simplified.

To protect the sensor system in the event of brief temperature changes, the metallic mount may be surrounded by a material, in particular by a synthetic material whose thermal conductivity is less than that of the mount material.

Normally the sensor system is protected by a plastic sheath made of a polymer or an elastomer, which of course leaves the depression for samples and the measuring surface free. The liquid sample taken and the sensor system are largely temperature-equalized independently of the ambient temperature due to the thermal contact in the depression for samples, and the refractive index is measured at this temperature. This temperature is measured simultaneously inside the refractometer in the area of the sensor system, preferably by a temperature sensor, in order to be able to take temperature influences into account and to refer the measurement result to a normalized temperature.

According to another advantageous embodiment of the present invention, the lens body or the glass body is made of a material having a refractive index which is greater than 1.5, in particular greater than 2. The refractive index of the lens is preferably 1.85.

A high refractive index of the glass body is advantageous when liquids also having high dielectric constants or refraction indices are to be measured.

The depression for samples advantageously has a volume of less than a milliliter for a particularly rapid temperature equalization.

The sensor system may be advantageously designed in that the radiation source is formed by an infrared LED and the beam detector is formed by a semiconductor which is sensitive in the infrared range.

Interference by external light is normally very small in the infrared range, and the components used operate reliably and relatively unaffected by errors.

The refractometer advantageously has a lens body which has an area having greater curvature, which faces the radiation source and the beam detector, and an area having lesser curvature which delimits the measuring surface.

This design of the lens body ensures optimal guidance of the measuring beam and optimum design of the measuring surface in terms of its metrological characteristics, the measuring surface also being easy to clean.

The present invention is elucidated in the following on the basis of an exemplary embodiment illustrated in the drawing.

DETAILED DESCRIPTION OF VARIOUS EMBODIMENTS

Figure 1:
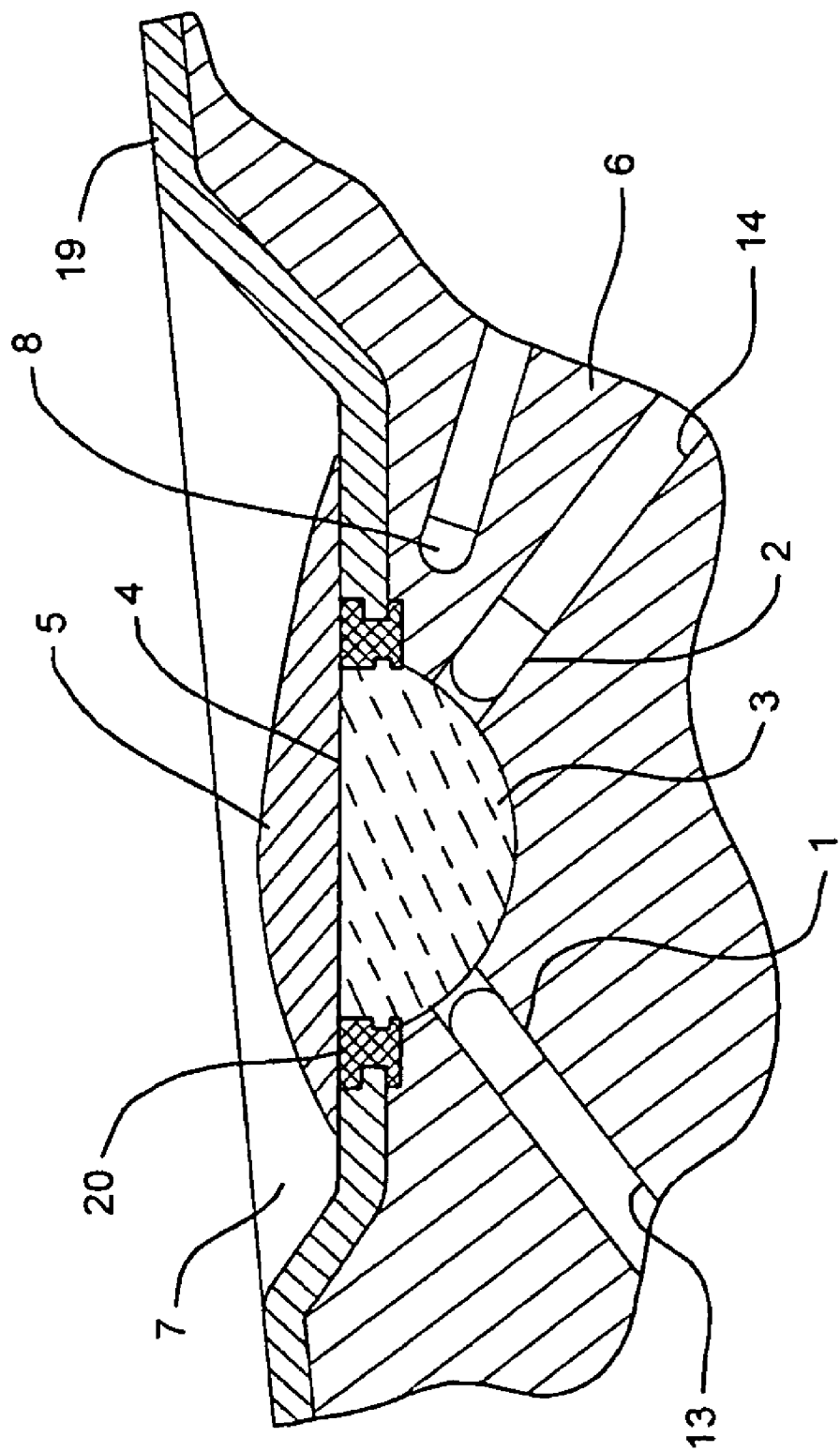
FIG. 1 schematically shows the internal structure of the sensor system.

Initially the operating principle of the refractometer according to the present invention will be elucidated on the basis of FIG. 1. The sensor system having radiation source 1 in the form of an infrared LED, beam detector 2 in the form of a light-sensitive semiconductor diode and the measuring path between them is schematically illustrated. A measuring beam is emitted from radiation source 1 to glass lens body 3 and enters, through its spherical or approximately spherical surface, perpendicularly into the glass body, through which it propagates to measuring surface 4, which is formed by a flat delimiting surface of lens body 3. The measuring beam is reflected or partly refracted there into the liquid as a function of the ratio between the refractive numbers (refractive indices) of the material of the lens body and the material of liquid 5 which wets the lens body.

At least one portion of the beam may be reflected on measuring surface 4 to beam detector 2 and detected by the latter.

The detected radiation intensity is measured using beam detector 2; it is a measure of the refractive index of liquid 5. The measurement is compared to a reference measurement, which has been made either without a wetting liquid on lens body 3 or using a known liquid, for determining the refractive number.

Due to the small aperture angle of beam detector 2, very little light reaches beam detector 2 from the outside through wetting liquid 5 and measuring surface 4, which permits the influence of external light on the measurement to be kept particularly low.

Due to the orientation of the lens, the measuring beam suffers little loss in entering into lens body 3 and exiting to the beam detector, while the flat design of measuring surface 4 makes the entry of external light into lens body 3 difficult. Cleaning of measuring surface 4 on the outside, which is exposed to liquids 5 to be measured is also facilitated by its flat design. The lens has typically a diameter of 3 mm and a refractive index greater than 1.5, in particular greater than 2.

Radiation source 1 and beam detector 2 are each situated in bore holes within mount 6, which fixedly and reliably determine their position with respect to one another and to lens body 3.

In addition, mount 6, which is made of metal, for example, steel or aluminum, ensures excellent heat conduction, so that elements 1, 2, 3 of the sensor system are reliably kept at the same temperature as mount 6, and the small size of the sample of liquid 5 ensures that the sample is very rapidly brought to the same temperature as mount 6 via heat transport thanks to glass lens body 3.

FIG. 1 shows, as an example, a small sample in the form of a drop of a liquid 5 on lens body 3; depression for samples 7 may also be regularly filled to the rim. In any case, temperature equalization between the sample and mount 6 takes only a few seconds. The depression for samples has a volume of less than 1 mL, in particular less than 0.5 mL.

Mount 6 is also provided with a temperature sensor 8 for temperature measurement, which permits temperature compensation when the measurements are analyzed.

Mount 6 is provided with a plastic layer 19, which insulates it thermally and thus protects the sensor system against varying external conditions. In the edge area of lens body 3, the lens body is sealed with respect to plastic layer 19 and mount 6 by elastic seals 20.

Figure 2:
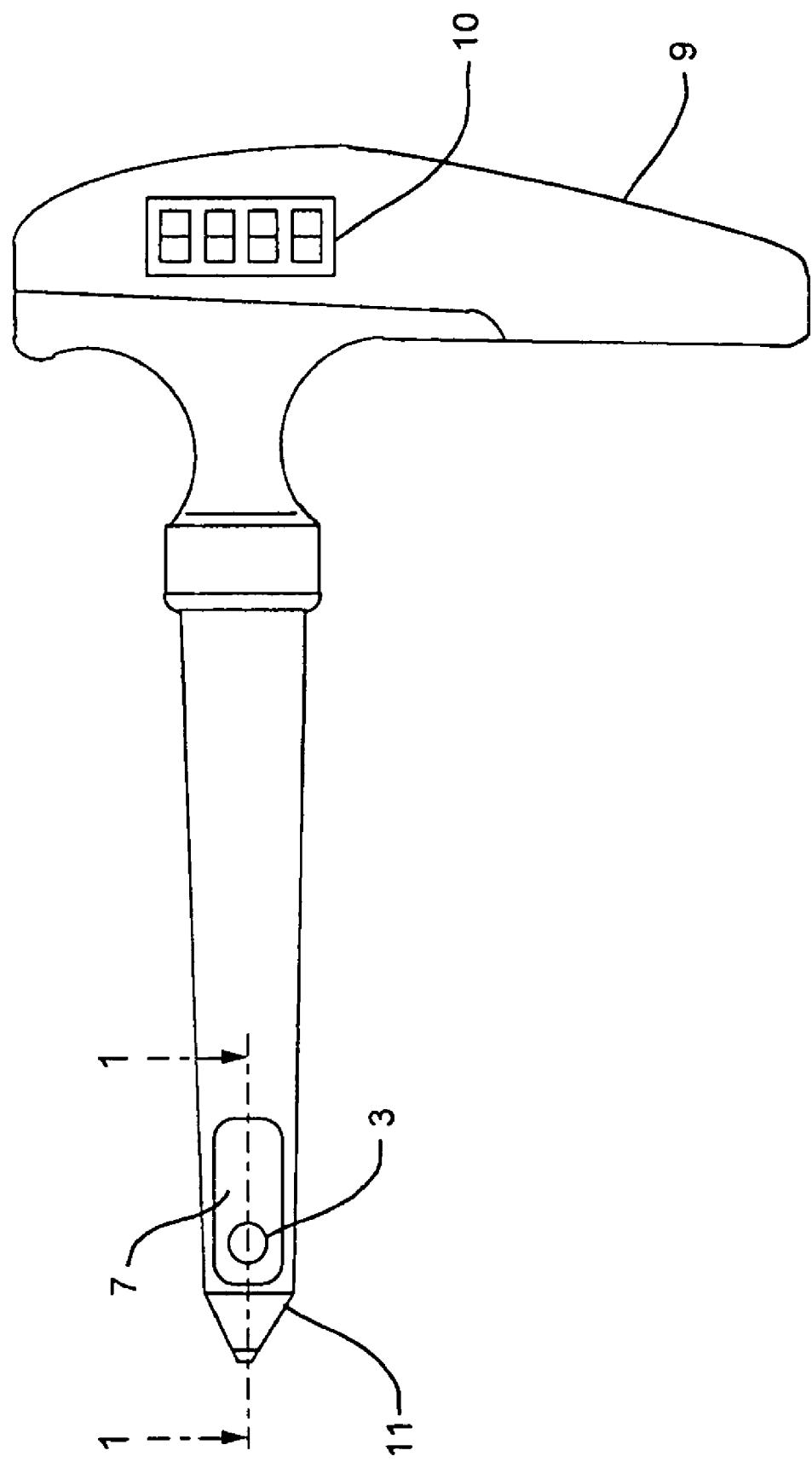
FIG. 2 schematically shows an insertion probe.

The schematic sectional view of FIG. 1 corresponds to a section along broken line A—A in FIG. 2, which is described in the following. FIG. 2 shows an external view of a portable refractometer having a handle 9, into which a digital display 10 is integrated. An analyzing device which analyzes the data delivered by beam detector 2 and temperature sensor 8 is mounted in the body of the portable refractometer. The sensor system is situated in the proximity of insertion tip 11, underneath depression for samples 7. In FIG. 2, lens body 3 is shown in the form of a circle.

Insertion tip 11 is designed so that it may be stuck into a fruit so that the fruit juice contained in the fruit enters depression for samples 7. However, it is also conceivable that insertion tip 11 is dipped into a liquid and that it has a groove-type notch on the top which leads to depression for samples 7 and allows the sample liquid to flow into depression for samples 7 even without insertion tip 11 being deeply dipped into the liquid or stuck into the fruit. Otherwise the insertion tip is introduced into the substance to be analyzed as deep as required for the depression for samples to be filled.

Figure 3:
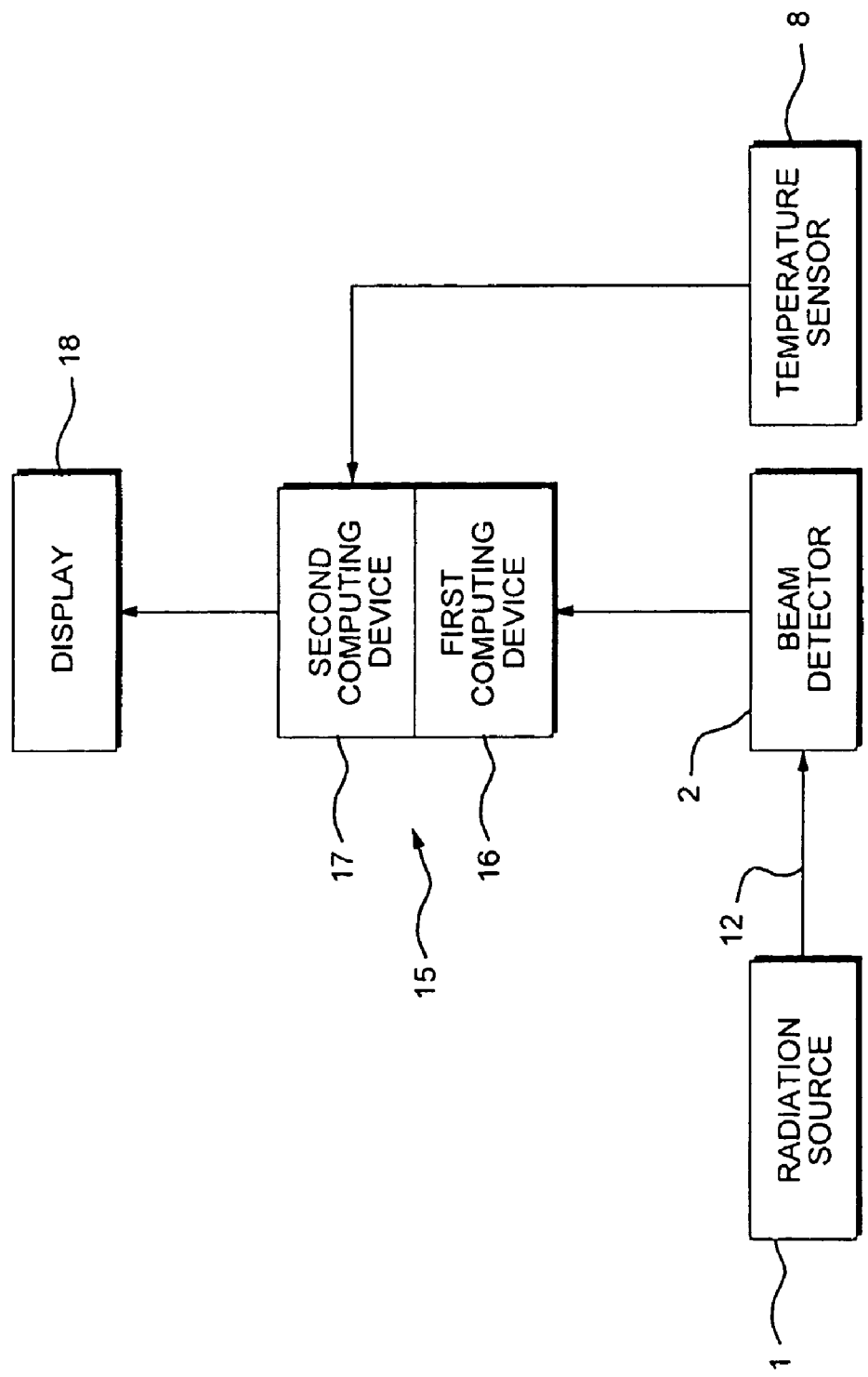
FIG. 3 shows an analyzer of the refractometer according to the present invention.

The mode of operation of the refractometer is now briefly elucidated schematically with reference to FIG. 3. Measuring beam 12 is generated by radiation source 1 in the form of an infrared beam, which propagates in the schematic representation of FIG. 1 along the central axis of mount hole 13, represented by a dot-and-dash line, in radiation source 1 to measuring surface 4, reflected there, and continues from there along the central axis of mount hole 14, also represented by a dot-and-dash line, in beam detector 2. The intensity of the reflected measuring beam 12 is measured in beam detector 2. The measured intensity is supplied to analyzer 15, where a value of the refractive index, i.e., refractive number, present is computed by a first computing device 16, initially without taking into account the temperature, using reference values. This value computed from the measurement is then referred to a reference temperature and thus compensated for the influence of temperature in second computing device 17, taking into account the temperature value measured by temperature sensor 8 and also provided by analyzer 15. The value of the refractive index, i.e., refractive number, computed and corrected in this way is then supplied to a display 18 and there output to the user via a digital display.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A refractometer for determining the refractive index of a liquid and variables derived therefrom, comprising: a sensor system, said sensor system including:
    a radiation source for generating a measuring beam, and
    a beam detector for detecting the measuring beam, the measuring beam running from the radiation source to a measuring surface to be wetted by the liquid, at least a portion of the measuring beam being reflected at said measuring surface and detected by the beam detector, wherein the measuring surface is situated in a depression for samples of an insertion probe which is insertable into the liquid.

2. The refractometer as recited in claim 1, wherein the measuring surface is formed by a boundary surface of a lens body.

3. The refractometer as recited in claim 1, wherein the measuring surface is formed by a boundary surface of a glass body.

4. The refractometer as recited in claim 2, wherein the radiation source the beam detector, and the lens body are held in a metallic mount.

5. The refractometer as recited in claim 4, wherein the metallic mount is surrounded by a synthetic material whose thermal conductivity is less than that of the mount material.

6. The refractometer as recited in claim 1, wherein a temperature sensor is provided in the area of the sensor system.

7. The refractometer as recited in claim 2, wherein the lens body is made of a material having a refractive index which is greater than 1.5.

8. The refractometer as recited in claim 1, wherein the volume of the depression for samples is less than 1 milliliter.

9. The refractometer as recited in claim 1, wherein the radiation source is formed by an infrared LED and the beam detector is formed by a semiconductor which is sensitive in the infrared range.

10. The refractometer as recited in claim 1, having a lens body which has an area having greater curvature and an area having lesser curvature of its surface, wherein the area having greater curvature faces the radiation source and the beam detector, and the area having lesser curvature delimits the measuring surface.

11. The refractometer as recited in claim 3, wherein the radiation source, the beam detector, and the glass body are held in a metallic mount.

12. The refractometer as recited in claim 4, wherein said metallic mount is made of steel or aluminum.

13. The refractometer as recited in claim 11, wherein said metallic mount is made of steel or aluminum.

14. The refractometer as recited in claim 3, wherein the glass body is made of a material having a refractive index which is greater than 1.5.

15. The refractometer as recited in claim 14, wherein said glass body is made of a material having a refractive index which is at least 2.0.

16. The refractometer as recited in claim 7, wherein said lens body is made of a material having a refractive index which is at least 2.0.

* * * * *